(12) United States Patent
Goutsis et al.

(10) Patent No.: US 10,300,002 B2
(45) Date of Patent: May 28, 2019

(54) DIRECT DYEING AGENTS IN FOAM FORM

(71) Applicant: Henkel AG & Co. KGaA, Duesseldorf (DE)

(72) Inventors: Konstantin Goutsis, Jüchen (DE); Gabriele Weser, Neuss (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 9 days.

(21) Appl. No.: 15/538,683

(22) PCT Filed: Nov. 2, 2015

(86) PCT No.: PCT/EP2015/075429
§ 371 (c)(1),
(2) Date: Jun. 22, 2017

(87) PCT Pub. No.: WO2016/102106
PCT Pub. Date: Jun. 30, 2016

(65) Prior Publication Data
US 2017/0354583 A1  Dec. 14, 2017

(30) Foreign Application Priority Data

Dec. 22, 2014 (DE) .................. 10 2014 226 752

(51) Int. Cl.
*A61Q 5/10* (2006.01)
*A61K 8/49* (2006.01)
*A61K 8/34* (2006.01)
*A61Q 5/06* (2006.01)
*A61K 8/04* (2006.01)
*A45D 19/02* (2006.01)
*A61K 8/81* (2006.01)

(52) U.S. Cl.
CPC ............ *A61K 8/4973* (2013.01); *A45D 19/02* (2013.01); *A61K 8/046* (2013.01); *A61K 8/34* (2013.01); *A61K 8/8182* (2013.01); *A61Q 5/065* (2013.01); *A61K 2800/30* (2013.01); *A61K 2800/432* (2013.01); *A61K 2800/87* (2013.01)

(58) Field of Classification Search
CPC ...... A61Q 5/065; A61K 8/4973; A61K 8/046; A61K 8/8182; A61K 2800/87; A61K 2800/432; A61K 2800/30; A61K 8/34; A45D 9/02
See application file for complete search history.

(56) References Cited

U.S. PATENT DOCUMENTS

| 6,099,828 A * | 8/2000 | Kajino ................. A61K 8/4913 132/208 |
| 2009/0178208 A1* | 7/2009 | Petzke ..................... A61K 8/31 8/408 |
| 2014/0298595 A1 | 10/2014 | Weser et al. |
| 2016/0287502 A1 | 10/2016 | Goutsis et al. |

FOREIGN PATENT DOCUMENTS

| DE | 19653496 A1 | 6/1997 |
| EP | 1237660 B1 | 8/2006 |
| JP | 61210023 A | 9/1986 |
| JP | 3577862 B2 | 10/2004 |
| WO | 2007083206 A1 | 7/2007 |
| WO | 2007086730 A2 | 8/2007 |
| WO | 2007086730 A3 | 8/2007 |
| WO | 2007091882 A1 | 8/2007 |

OTHER PUBLICATIONS

EPO, International Search Report and Written Opinion issued in International Application No. PCT/EP/2015/075429, dated Jan. 27, 2016.

* cited by examiner

*Primary Examiner* — Eisa B Elhilo
(74) *Attorney, Agent, or Firm* — Lorenz & Kopf, LLP

(57) ABSTRACT

A cosmetic composition for dyeing keratinous fibers is provided herein. The cosmetic composition includes water and from about 6 to about 12 wt % organic solvent relative to the weight of the composition. The organic solvent includes from about 80 to about 100 wt % propylene carbonate and from about 0 to about 20 wt % benzyl alcohol. The cosmetic composition has a pH value in the range from about 1.0 to about 5.5 and at least one acid directly absorbed dye.

18 Claims, No Drawings

DIRECT DYEING AGENTS IN FOAM FORM

CROSS-REFERENCE TO RELATED APPLICATION

This application is a U.S. National-Stage entry under 35 U.S.C. § 371 based on International Application No. PCT/EP2015/075429, filed Nov. 2, 2015 which was published under PCT Article 21(2) and which claims priority to German Application No. 102014226752.8, filed Dec. 22, 2014, which are all hereby incorporated in their entirety by reference.

TECHNICAL FIELD

The object of the present application is a composition for dyeing keratinous fibers, particularly human hair, which is adjusted to an acidic pH and contains at least one direct-dyeing acid colorant and a special mixture of two organic solvents which are designed to be discharged from special application devices in the form of a stable foam. A further object of the present application is a method for dyeing keratin fibers, in which a corresponding composition is applied to keratinous fibers.

BACKGROUND

Changing the shape and color of keratinous fibers, particularly hair, is an important area of modern cosmetics. In this way, the appearance of hair can be changed to reflect both current fashion trends and the personal desires of an individual. Coloring, particularly covering grey hair, is desired by many people.

Various coloring systems for changing the color of hair are known the person skilled in the art, depending on the requirement the coloring must meet. For permanent, intense colors with good fastness properties and good grey coverage, as a rule oxidizing dyes are used. Such dyes typically contain oxidation dye precursors, "also called primary and secondary intermediates", which combine to form the actual dyes under the effects of oxidizing compositions such as hydrogen peroxide. Oxidation dyes are characterized by excellent, long-lasting coloring, but are also associated with a certain quantity of hair damage.

Hair color can be changed temporarily through the use of directly absorbed dyes. In these cases, already fully prepared colorants diffuse from the dye into the hair fibers. In order to improve dye diffusion, it is common to add one or more organic solvents to the colorant recipe, such solvents being selected from lower alkylene carbonates, e.g., propylene carbonate, aromatic alcohols, particularly benzyl alcohol, phenoxyethanol or benzyloxyethanol, and N-alkylpyrrolidones, particularly N-methylpyrrolidone.

Compared to oxidation hair dyeing, the coloring results obtained with directly absorbed dyes do not last as long and wash out sooner. The grey coverage achievable with directly absorbed dyes generally also needs improvement. However, one advantage is that less damage is caused to the hair by directly absorbed dyes. Consequently, the use of directly absorbed dyes is the dyeing method of choice in order to minimize hair damage.

Direct-dyeing colorants are often formulated and marketed as shampoo preparations. Many attempts have also been made to develop other packaging forms. For example, it has been suggested to apply thinner colorant in the form of a foam. Particularly in the case of foam application, the use of aerosol foams is widespread.

A problem with foam application is that of stabilizing the foams. The consistency of foams is described as ideal when a firm, stable foam is formed upon dispensing which leaves a silky feeling and only breaks slowly on the hair. However, it has often been found that the foams delivered are unstable and quickly collapse back into themselves, so that a low-viscosity, dripping solution remains. On the other hand, it is also essential that the foam still wets the hair thoroughly to ensure good dye coverage. The stability of the foam is particularly adversely affected by the presence of large quantities of organic solvents.

Hair dyes in foam form for direct hair coloring containing from about 5 to about 65 wt % organic solvents including low alkylene carbonates and aromatic alcohols as particularly suitable solvents have been disclosed previously in patent document JP61210023A. Foam hair dyes for direct hair coloring which disclose aromatic alcohols and N-alkyl pyrrolidones as particularly suitable solvents are known from German patent DE19653496A1.

However, the foaming properties of the foams produced thereby were still not entirely satisfactory, particularly with respect to the breaking of the foam when it is spread on the hair, in order to ensure optimal distribution of the coloring composition and optimal impregnation of the dye by the hair.

BRIEF SUMMARY

A cosmetic composition for dyeing keratinous fibers is provided herein. The cosmetic composition includes water and from about 6 to about 12 wt % organic solvent relative to the weight of the composition. The organic solvent includes from about 80 to about 100 wt % propylene carbonate and from about 0 to about 20 wt % benzyl alcohol. The cosmetic composition has a pH value in the range from about 1.0 to about 5.5 and at least one acid directly absorbed dye.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object underlying the present disclosure is to provide direct dyeing of keratin fibers which is discharged as foam from a dispenser and is then applied to the hair as a foam and enables coloring with good washing fastness to washing and good grey coverage.

Now it has now been found that keratin fibers can be dyed intensely with a composition that is adjusted to an acidic pH and contains at least one acid directly absorbed dye and contains from about 6 to about 12 wt % organic solvent relative to the weight of the composition, wherein the solvent consists of about 80-100 wt % propylene carbonate and about 20-0 wt % benzyl alcohol.

When this composition is used as the foam, optimal foam quality is obtained, the foam is sufficiently stable to be spread evenly through the hair, but then also breaks fast enough to ensure optimum color take-up.

A first object of the present disclosure is an aqueous cosmetic composition for dyeing keratinous fibers, which has
  a pH value in the range from about 1.0 to about 5.5 and
  at least one acid directly absorbed dye and and contains from about 6 to about 12 wt % organic solvent relative to the weight of the composition, which solvent consists of from about 80 to about 100 wt % propylene carbonate and from about 0 to about 20 wt % benzyl alcohol.

The terms keratinous fibers, keratin-containing fibers or keratin fibers are understood to refer to furs, wool, feathers, and particularly human hair. Although the compositions as contemplated herein are primarily designed for dyeing keratin fibers, theoretically there is nothing to prevent them from being used in other areas as well.

The composition as contemplated herein is a water-containing cosmetic product.

Preferred compositions contain from about 60 to about 90 wt % of water, preferably from about 70 to about 87 wt % water relative to the weight of the composition.

As a first essential ingredient, the composition as contemplated herein contains at least one acid directly absorbed dye.

Direct-dyeing colorants can be divided into cationic dyes (basic dyes), nonionic dyes and anionic dyes (also called acid dyes) according to their charge.

Direct-dyeing colorants that have at least one carboxylic acid group (—COOH) and/or a sulphonic acid group (—SO$_3$H) are understood to be acid dyes. The protonated forms (—COOH, —SO$_3$H) of the carboxylic acid or sulphonic acid groups are in equilibrium with their deprotonated forms (—COO$^-$, —SO$_3^-$) depending on the pH value. As the pH falls, the proportion of the protonated forms rises. If direct dyeing colorants are used in the form of their salts, the carboxylic acid groups or sulphonic acid groups are in deprotonated form and are neutralized to maintain electroneutrality with corresponding stoichiometric equivalency of cations (such as Na cation or K cation).

An essential feature of the acid dyes is their ability to form anionic charges, wherein the carboxylic acid or sulphonic acid groups responsible for this may be linked to different chromophoric systems. Suitable chromophoric systems are found for example in the structures of azo dyes, triarylmethane dyes, anthraquinone dyes, xanthene dyes and rhodamine dyes and/or oxazine dyes.

One or more compounds may be selected for example from the following group as suitable acid dyes: Acid Yellow 1 (D&C Yellow 7, citronin A, Ext D&C Yellow No. 7, Japan Yellow 403, CI 10316, COLIPA no. B001), Acid Yellow 3 (Colipa no.: C54, D&C Yellow no. 10, Quinoline Yellow, E104, Food Yellow 13), Acid Yellow 9 (CI 13015), Acid Yellow 17 (CI 18965), Acid Yellow 23 (Colipa no. C29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-naphthol orange, Orange II, CI 15510, D&C Orange 4, COLIPA no. C015), Acid Orange 10 (CI 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodiumsalt; Brown No. 201; RESORCINOL BROWN; ACID ORANGE 24; Japan Brown 201; D&C Brown No. 1), Acid Red 14 (CI 14720), Acid Red 18 (E124, Red 18; CI 16255), Acid Red 27 (E 123, CI 16185, C-Red 46, True Red D, FD&C Red No. 2, Food Red 9 naphthol red S), Acid Red 33 (Red 33, Fuchsia Red, D&C Red 33, CI 17200), Acid Red 35 (CI C.I. 18065), Acid Red 51 (CI 45430, Pyrosin B, Tetraiodofluorescein, Eosin J, Iodeosin), Acid Red 52 (CI 45100, Food Red 106, Solar Rhodamine B, Acid Rhodamine B, Red no. 106 Pontacyl Brilliant Pink), Acid Red 73 (CI CI 27290), Acid Red 87 (Eosin, CI 45380), Acid Red 95 (CI 45425, Erythtosine, Simacid Erythrosine Y), Acid Red 184 (CI 15685), Acid Red 195, Acid Violet 43 (Jarocol Violet 43, Ext. D&C Violet no. 2, C.I. 60730, COLIPA no. C063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133 Patent Blue AE, Amidoblau AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreenl) Acid Green 5 (CI 42095), Acid Green 9 (C.I. 42100), Acid Green 22 (C.I. 42170), Acid Green 25 (CI 61570, Japan Green 201, D&C Green No. 5), Acid Green 50 (Acid Brilliant Green BS, CI 44090, Acid Brilliant Green BS, E 142), Acid Black 1 (Black no. 401, Naphthalene Black 10B, Amido Black 10B, CI 20470, COLIPA no. B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

A particularly preferred composition as contemplated herein is therefore characterized in that it contains at least one directly absorbed dye acid dye from the group Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 18, Acid Red 27, Acid Red 33, Acid Red 35, Acid Red 51, Acid Red 52, Acid Red 73, Acid Red 87, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 7, D&C Yellow 8, D&C Orange 4, D&C Green 5, D&C Orange 10, D&C Orange 11, D&C Red 21, D&C Red 27, D&C Red 33, D&C Violet 2 and/or D&C Brown 1.

It has been found that certain acid dyes, particularly certain combinations of acid dyes, are particularly well suited for use on damaged hair, as they are absorbed into the damaged keratin fibers particularly well, where they lead to exceptionally intense color results. The following dye combinations are absorbed particularly well by damaged keratin fibers: Acid Yellow 1/Acid Orange 7; Acid Yellow 3/Acid Orange 7; Acid Yellow 9/Acid Orange 7; Acid Yellow 17/Acid Orange 7; Acid Yellow 23/Acid Orange 7; Acid Yellow 36/Acid Orange 7; Acid Yellow 121/Acid Orange 7; Acid Red 14/Acid Orange 7; Acid Red 18/Acid Orange 7; Acid Red 27/Acid Orange 7; Acid Red 33/Acid Orange 7; Acid Red 35/Acid Orange 7; Acid Red 51/Acid Orange 7; Acid Red 52/Acid Orange 7; Acid Red 73/Acid Orange 7; Acid Red 87/Acid Orange 7; Acid Red 95/Acid Orange 7; Acid Red 184/Acid Orange 7; Acid Red 195/Acid Orange 7; Acid Violet 43/Acid Orange 7; Acid Violet 49/Acid Orange 7 and/or Acid Violet 50/Acid Orange 7.

A further most particularly preferred composition as contemplated herein is therefore characterized in that it contains at least one of the following combinations of acid directly absorbed dyes: Acid Yellow 1/Acid Orange 7; Acid Yellow 3/Acid Orange 7; Acid Yellow 9/Acid Orange 7; Acid Yellow 17/Acid Orange 7; Acid Yellow 23/Acid Orange 7; Acid Yellow 36/Acid Orange 7; Acid Yellow 121/Acid Orange 7; Acid Red 14/Acid Orange 7; Acid Red 18/Acid Orange 7; Acid Red 27/Acid Orange 7; Acid Red 33/Acid Orange 7; Acid Red 35/Acid Orange 7; Acid Red 51/Acid Orange 7; Acid Red 52/Acid Orange 7; Acid Red 73/Acid Orange 7; Acid Red 87/Acid Orange 7; Acid Red 95/Acid Orange 7; Acid Red 184/Acid Orange 7; Acid Red 195/Acid Orange 7; Acid Violet 43/Acid Orange 7; Acid Violet 49/Acid Orange 7 or Acid Violet 50/Acid Orange 7.

The acid directly absorbed dyes are preferably contained in a total quantity of from about 0.01 to about 5.5 wt %, preferably from about 0.08 to about 4.7 wt %, more preferably from about 0.2 to about 3.4 wt % and particularly preferably from about 0.3 to about 1.8 wt % relative to the weight of the composition respectively. Especially when the total content is equal to from about 0.3 to about 1.8 wt % relative to the weight of the composition, very intense dyeing results can be achieved without the composition causing excessive skin staining. A most particularly preferred composition as contemplated herein is therefore characterized in that it contains one or more acid directly absorbed dyes in a total quantity of from about 0.01 to about 5.5 wt %, preferably from about 0.08 to about 4.7 wt %, more preferably from about 0.2 to about 3.4 wt % and particularly preferably from about 0.3 to about 1.8 wt %—relative to the total weight of the composition.

Acid dyes typically require an acidic medium in order to be absorbed into the keratin fibers. To ensure sufficient color absorption of the acid directly absorbed dyes, the compositions as contemplated herein must be adjusted to an acidic pH. In this context, the more acidic the medium the better the acid directly absorbed dyes are absorbed. A pH-value up to about 5.5 is suitable, although the intensity of the color is exceedingly more intense if the pH of the medium is set at a value up to a maximum of about 4.7, preferably about 3.9, more preferably to a maximum of about 3.1 and very particularly preferably to a maximum about 2.5. For toxicological reasons, it is not appropriate to adjust the compositions to pH values of less than about 1.0. The pH of the composition is preferably not less than about 1.5, more preferably not below about 1.7, and most preferably not less than about 1.8.

A further most particularly preferred composition as contemplated herein is therefore characterized in that it has a pH value from about 1.5 to about 4.7, preferably from about 1.6 to about 3.9, more preferably from about 1.7 to about 3.1 and particularly preferable from about 1.8 to about 2.5.

In principle, all compounds that are capable of donating one proton (monobasic acid) or more protons (polybasic acid) are suitable for use in adjusting the acidic pH values. Regarding inorganic acids, for example, mineral acids such as hydrochloric acid, sulphuric acid and phosphoric acid are used, preferably in a form diluted with water. Organic acids may also be used in the inventive formulations. Typical representatives of organic acids are aliphatic mono- and dicarboxylic acids such as acetic acid, propionic acid, oxalic acid and 1,3-propanedioic and aromatic carboxylic acids such as benzoic acid. Further organic acids as contemplated herein are hydroxycarboxylic acids such as glycolic acid, citric acid, tartaric acid, malic acid and lactic acid. Unsaturated mono- or dicarboxylic acids such as fumaric acid or alpha-keto carboxylic acids such as pyruvic acid (2-oxopropanoic acid) are suitable for the purposes as contemplated herein.

However, in view of the technical and legal requirements which govern formulations of cosmetic products, low-odor acids that are already approved for use in cosmetics are best suited for the development of hair treatment compositions with good dyeing performance. Hair dyes containing at least one acid selected from citric acid, tartaric acid, malic acid, lactic acid, 1-hydro xyethan-1,1-diphosphonic acid, 2,6-dipicolinic acid and benzoic acid are therefore preferred. The pH-values that were measured for the purposes of this disclosure are pH values measured at a temperature of 22° C. Glass electrodes, which can be configured in the form of a combination electrode, for example, are particularly suitable for measuring the pH. Observance of the suitable, preferred and particularly preferred pH ranges listed above is essential in order to achieve satisfactory dyeing results. It has further been found that in in order to achieve optimum reduction of hair damage, it is important to adjust pH reliably to the desired and preferred ranges. In order to maintain the adjusted pH in the desired range for long periods as well, the additional use of buffers i.e., use of a weak acid (e.g., acetic acid) with a completely dissociated salt of the same acid (e.g., sodium acetate) is therefore particularly preferable. Certain buffer systems have shown particular suitability here.

A further most particularly preferred composition as contemplated herein is therefore characterized in that it contains at least a mixture of an acid and the alkali salt of said acid, wherein the acid is selected from the group citric acid, tartaric acid, malic acid, lactic acid and 1-hydroxyethane-1,1 diphosphonic acid.

The term citric acid (alternative name: 2-hydroxypropane-1,2,3-tricarboxylic acid) is understood to include the D-form of the acid, the L-form of the acid and the mixtures thereof.

Tartaric acid (alternative names: 2,3-dihydroxybutanedioic acid, 2,3-dihydroxysuccinic acid) occurs in three stereoisomeric forms: the enantiomer L-(+)-tartaric acid and D-(−)-tartaric acid, as well as the optically inactive meso-form. All of these stereoisomeric forms of tartaric acid and mixtures thereof are suitable for use as contemplated herein.

Malic acid (alternative names: hydroxybutanedioic acid, hydroxysuccinic acid) exists in a R-(+)-form and the enantiomeric S-(−) form, and mixtures thereof are suitable for use.

The term lactic acid (alternative names: 2-hydroxypropanoic acid, 2-hydroxypropionic acid) is understood to include the D-form of the acid, the L-form of the acid and mixtures thereof.

The aforementioned acids are monobasic acids (such as lactic acid) or polybasic acids (citric acid, tartaric acid, malic acid). As contemplated herein, the alkali salts of these acids are understood to be the monovalent or polyvalent (in the case of the polybasic acids) potassium and sodium salts of these acids.

Accordingly, it is also very particularly preferable for a water-containing cosmetic composition for dyeing keratinous fibers
- to have a pH in the range from about 1.0 about to 5.5,
- to contain at least one acid directly absorbed dye,
- to contain from about 6 to about 12 wt % organic solvent relative to the weight of the composition, which solvent consists of from about 80 to about 100 wt % propylene carbonate and about 0-20 wt % benzyl alcohol, and
- a mixture of an acid and the alkaline salt of the same acid, wherein the acid is selected from the group citric acid, tartaric acid, malic acid, lactic acid and 1-hydroxyethane-1,1-diphosphonic acid.

For reproducible and reliable stabilization of pH, particularly suitable buffer systems have been found to be those which consist of a mixture of the following acids and their salts:
- Lactic acid and a sodium salt of lactic acid, and/or
- Lactic acid and a potassium salt of lactic acid,
- Citric acid and a sodium salt of citric acid, Citric acid and a potassium salt of citric acid,
Tartaric acid and a sodium salt of tartaric acid,
Tartaric acid and a potassium salt of tartaric acid,
1-hydroxyethane-1-1-disphosphonic acid and a sodium salt of 1-hydroxy ethane-1-1-disphosphonic acid,
1-hydroxyethane-1-1-disphosphonic acid and a potassium salt of 1-hydroxyethane-1-1-disphosphonic acid.

The compositions as contemplated herein also contain from about 6 to about 12 wt % organic solvent relative to the weight of the compositions, as a further essential ingredient, wherein the solvents consist of about 80-100 wt % propylene carbonate and about 0-20 wt % benzyl alcohol.

It is common knowledge in the prior art that the color take-up of acid directly absorbed dyes by keratin fibers can be further improved by use of an organic solvent. Here, certain solvents have been found to be particularly suitable. For example, the color take-up of acid dyes could not be improved with the use of isopropanol and other aliphatic alcohols such as ethanol. But aromatic alcohols but such as benzyl alcohol, result in a significant gain of color intensity.

Benzyl alcohol is an aromatic alcohol with formula (I).

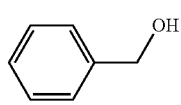

(I)

Propylene carbonate is alternatively called 4-methyl-1,3-dioxolane-2-one and has the structure of formula (II).

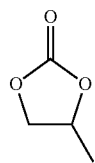

(II)

Both benzyl alcohol alone and propylene carbonate alone yield excellent coloring results. However, propylene carbonate is a significantly more expensive raw material than benzyl alcohol, so preferably a composition should be used that contains as little propylene carbonate as possible without sacrificing the coloring result or the application properties.

It was observed that the selection of the organic solvent for improving the color take-up of the acid directly absorbed dye is critical for the stability of the foam. It was found that the total content of organic solvent must be from about 6 to about 12 wt %, preferably from about 10 to about 12 wt % relative to the weight of the composition respectively in order to achieve good color absorption and high quality dyeing result. The use of about 10 wt % benzyl alcohol alone, however, had an unacceptably adverse effect on foam stability.

The use of 10 wt % propylene carbonate alone gave both excellent coloring results and very good foam stability. The extent to which the propylene carbonate could be replaced with benzyl alcohol for financial reasons was also investigated. It was found that optimal dyeing results together with optimal foam properties were obtained with a composition that contains from about 6 to about 12 wt %, preferably about 10-12 wt % organic solvent relative to the weight of the composition, wherein the solvent consists of about 80-100 wt %, preferably about 85-97 wt % propylene carbonate and about 0-20 wt %, preferably about 3-15 wt % benzyl alcohol respectively relative to the weight of the organic solvent.

Converted to absolute quantities, this means that the compositions as contemplated herein contain about 4.8-12 wt %, preferably about 8-10 wt % and particularly preferably from about 8.5 to about 9.6 wt % propylene carbonate and about 0-2.4 wt %, preferably about 0.18-2.0 wt %, particularly preferably about 1.0-1.8 wt % benzyl alcohol relative to the total weight of the composition respectively.

In a particularly preferred embodiment, the inventive compositions contain neither 2-phenoxyethane-1-ol nor benzyloxyethanol nor N-alkyl pyrrolidones.

The inventive composition is designed specifically for the use of acid directly-absorbed dyes, and accordingly the exclusive use of acid directly-absorbed dyes (i.e. dyes which support carboxylic acid and/or sulphonic acid groups, which can also be used in the form of their salts) is also preferred. In other words, it is preferred if the colorant as contemplated herein contains:
no nonionic nitro dyes
no nonionic azo dyes
no nonionic anthraquinone dyes
no cationic anthraquinone dyes, an
no cationic triarylmethane dyes.

A preferred composition as contemplated herein is further characterized in that it comprises—relative to its weight—less than about 0.4 wt %, preferably less than about 0.25 wt %, more preferably less than about 0.1 wt % and most preferably contains less than about 0.05 wt % non-ionic dyes.

In this context, nonionic dyes are understood to include dyes whose structure does not have an acid group (—COOH), a carboxyl group (COO), a sulphonic acid group (—$SO_3H$) or a sulphonate group (—$SO_3$) and whose structure also does not have a functional group with permanent cationic charge (such as a quaternary ammonium group).

A preferred composition as contemplated herein is further characterized in that it contains the nonionic dyes from the group of HC Yellow 2, HC Yellow 4, HC Yellow 5, HC Yellow 6, HC Yellow 12, HC Orange 1, Disperse Orange 3, HC Red 1 HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-diamino-2-nitrobenzene, 2-amino-4-nitrophenol, 1,4-bis(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino] benzoic acid, 6-nitro-1,2,3,4-tetrahydroquinoxaline, 2-hydroxy-1,4-naphthalene thoquinone, picramic acid and salts thereof, 2-amino-6-chloro-4-nitrophenol, 4-ethylamino-3-nitro-benzoic acid and 2-chloro-6-ethylamino-4-nitrophenol in a total quantity of less than 0.4 wt %, preferably less than 0.25 wt %, more preferably less than 0.1 wt % and particularly preferably less than 0.05 wt %, relative to the weight of the composition in each case.

A further preferred composition as contemplated herein is characterized in that it contains less than about 0.4 wt %, preferably less than about 0.25 wt %, more preferably less than about 0.1 wt % and particularly preferably less than about 0.05 wt % cationic dyes relative to the weight of the composition in each case.

A preferred composition as contemplated herein is further characterized in that it contains the cationic directly absorbed dyes from the group Basic Blue 7, Basic Blue 26, Basic Violet 2, Basic Violet 14, Basic Yellow 57, Basic Red 76, Basic Blue 99, Basic Brown 16, Basic Brown 17, HC Blue 16, Basic Yellow 87, Basic Orange 31 and Basic Red 51 in a total quantity of less than 0.4 wt %, preferably less than 0.25 wt %, more preferably less than 0.1 wt % and particularly preferably less than 0.05 wt %, each relative to the weight of the composition.

The inventive composition preferably has the form of a surfactant-containing solution, such as a shampoo or conditioner, which can be frothed by introducing air or a propellant such as LPG or dimethyl ether.

For the purposes of the present application surfactants and emulsifiers are amphiphilic (bifunctional) compounds consisting of at least one hydrophobic and at least one hydrophilic moiety. The hydrophobic radical is preferably a hydrocarbon chain with 8-28 carbon atoms which may be saturated or unsaturated, linear or branched. Particularly preferably, this C8-C28 alkyl chain is linear. Basic features of surfactants and emulsifiers are oriented absorption at boundary surfaces and aggregation into micelles and the formation of lyotropic phases.

Therefore, compositions as contemplated herein preferably also contain at least one cationic surfactant in a total quantity from about 0.1 to about 2 wt %, preferably about 0.2-1.5 wt %, particularly preferably about 0.4-0.8 wt %, relative to the weight of the composition respectively.

Preferred as contemplated herein are cationic surfactants of the quaternary ammonium compound type, esterquats and alkyl amidoamines. Preferred quaternary ammonium compounds are ammonium halides, such as alkyltrimethylammonium chlorides, dialkyldimethylammonium chlorides, trialkylmethylammonium chlorides, and the imidazolium compounds known by the INCI names Quaternium-27 and Quaternium-83. Further preferred quaternary ammonium compounds are tetraalkylammonium salts, in particular those known by the INCI designation quaternium-52, a poly(oxy-1,2-ethanediyl), ((Octadecylnitrilio)tri-2,1-ethanediyl)tris(hydroxy) phosphate (1:1) salt having general structural formula (III) wherein x+y+z=10

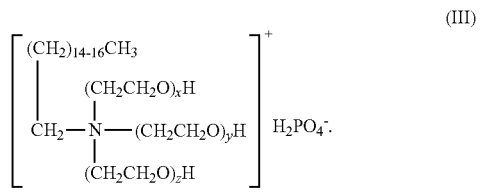

The long alkyl chains of the abovementioned surfactants preferably have 10 to 22, particularly preferably 12 to 18 carbon atoms. Particularly preferred are behenyl trimethylammonium chloride, stearyl trimethylammonium chloride and cetyl trimethylammonium chloride, wherein cetyl trimethylammonium chloride which is preferred by far. Further suitable cationic surfactants as contemplated herein are quaternized protein hydrolysates. Alkylamidoamines are usually produced by amidation of natural or synthetic fatty acids and fatty acid cuts with dialkylaminoamines. An inventively suitable compound from this group of substances is Tegoamid® S 18 (stearamidopropyl dimethylamine). Esterquats are substances which contain both at least one ester function and at least one quaternary ammonium group as a structural element. Preferred esterquats are quaternized ester salts of fatty acids with triethanolamine, quaternized ester salts of fatty acids with diethanol alkyl amines and quaternized ester salts of fatty acids with 1,2-dihydroxypropyldialkylamines. Such products are sold under the trade names Stepantex, Dehyquart and Armocare.

Regarding optimal foaming properties and optimal coloring results, C10-C22 alkyl trimethyl ammonium chlorides and quaternium-52 as well as mixtures of these surfactants have been found to be particularly suitable. Particularly preferred compositions as contemplated herein are therefore characterized in that they comprise at least one cationic surfactant in a total quantity from about 0.1 to about 2% by weight, preferably from about 0.2 to about 1.5 wt %, particularly preferably from about 0.4 to about 0.8 wt % relative to the weight of the respective composition, wherein at least one surfactant selected from C10-C22 alkyltrimethylammonium chlorides, particularly selected from behenyl trimethyl ammonium chloride, stearyl trimethyl ammonium chloride and cetyl trimethyl ammonium chloride, and quaternium-52 and mixtures of these surfactants, are included. By far the most preferred compositions contain cetyl trimethyl ammonium chloride and quaternium-52 in a total quantity from about 0.1 to about 2 wt %, preferably from about 0.2 to about 1.5 wt %, particularly preferably from about 0.4 to about 0.8 wt %, relative to the weight of the respective composition.

Further preferred compositions as contemplated herein are characterized in that they contain at least one nonionic ethoxylated surfactant in a total quantity from about 0.1 to about 1 wt %, preferably about 0.2-0.8 wt %, particularly preferably from about 0.3 to about 0.7 wt %, relative to the weight of the composition respectively.

Nonionic surfactants contain for example, a polyol group, a polyalkylene glycolether group or a combination of polyol and polyglycol groups as the hydrophilic group. The ethylene oxide adducts to saturated or unsaturated, linear or branched fatty alcohols and fatty acids and to glycerol fatty acid esters, each with from about 2 to about 60 moles ethylene oxide per mole fatty alcohol or fatty acid or glycerol fatty acid esters and mixtures thereof have been found to be preferred nonionic surfactants. Especially preferred as contemplated herein are saturated or unsaturated $C_{10}$-$C_{22}$ fatty alcohols each with from about 10 to about 25 moles ethylene oxide per mole fatty alcohol (e.g. Ceteareth-20 or Ceteareth-25). Very highly preferred nonionic surfactants are selected from PEG-40 Hydrogenated Castor Oil and PEG-60 Hydrogenated Castor Oil and mixtures thereof. These particularly preferred nonionic surfactants are extremely well suited to solubilizing the organic solvent phase and thus contribute positively to both the dyeing and the foaming behavior. Thus these surfactants function extremely well in solubilizing optionally present fragrance, which is preferably contained in a total quantity of from about 0.05 to about 0.5 wt % relative to the weight of the composition. Further preferred compositions as contemplated herein contain at least one amphoteric or zwitterionic surfactant or mixtures thereof.

Zwitterionic surfactant is the term used to describe surface-active compounds which carry at least one quaternary ammonium group and at least one carboxylate, sulphonate or sulphate group in the molecule. Particularly suitable zwitterionic surfactants are the "betaines" such as the N-alkyl-N,N-dimethylammonium glycinates, N-acylaminopropyl-N,N-dimethylammonium glycinates, and 2-alkyl-3-carboxymethyl-3-hydroxyethyl-imidazolines and cocacylaminoethyl hydroxyethyl carboxymethyl glycinate.

A preferred zwitterionic surfactant is the fatty acid amide derivative known by its INCI name Cocoamidopropyl Betaine. In a further embodiment of the present disclosure, the composition further contains at least one amphoteric surfactant. Amphoteric surfactants are understood to be those surface-active compounds which, apart from a $C_8$-$C_{24}$ alkyl or acyl group in the molecule contain at least one free amino group and at least one COOH— or $SO_3H$ group and are capable of forming inner salts. Examples of suitable amphoteric surfactants are N-alkyl glycines, N-alkyl propionic acids, N-alkylamino butyric acids, N-alkylimino-dipropionic acids, N-hydroxyethyl-N-alkylamido propyl glycines, N-alkyltaurines, N-alkylsarcosines, 2-alkylaminopropionic acids and alkylaminoacetic acids. Particularly preferred amphoteric surfactants are marketed with INCI designator Disodium Cocoamphodipropionate under the trade names Miranol C2M SF conc. (Rhodia), Amphoterge K-2 (Lonza) and Monateric CEM-38 (Unichema) and with INCI designator Disodium Cocoamphodiacetate under the tradenames Dehyton (Cognis), Miranol C2M (Rhodia) and Ampholak XCO 30 (Akzo Nobel).

The inventive compositions may optionally also contain at least one anionic surfactant. All anionic surfactants that are suitable for use on the human body also lend themselves to use as anionic surfactants in preparations as contemplated herein. These are characterized by a water solubilizing anionic group such as a carboxylate, sulphate, sulphonate or phosphate group and a lipophilic alkyl group having from about 8 to about 30 carbon atoms, preferably from about 8 to about 24 carbon atoms. In addition, glycol or polyglycol ether groups, ester, ether and amide groups as well as hydroxyl groups may be contained in the molecule. Preferred anionic surfactants are soaps, alkyl sulphates, alkyl ether sulphates and ether carboxylic acids having from about 8 to about 22 carbon atoms in the alkyl group and up to about 12 glycol ether groups in the molecule.

However, since a content of cationic surfactants as described above is preferred as contemplated herein, and this may result in undesirable interaction, agglomeration for example, when cationic and anionic surfactants are present simultaneously, particularly preferred compositions are characterized in that no anionic surfactants are contained.

Further particularly preferred compositions as contemplated herein are characterized by a total surfactant content of from about 0.5 to about 2 wt %, preferably from about 0.7 to about 1.5 wt %, particularly preferably from about 0.8 to about 1.2 wt %, relative to the respective weight of the composition.

Further particularly preferred compositions as contemplated herein may contain one or more cationic polymers from the group polyquaternium-1, polyquaternium-2, polyquaternium-3, polyquaternium-4, polyquaternium-5, polyquaternium-6, polyquaternium-7, Polyquaternium-8, Polyquaternium-9, Polyquaternium-10, Polyquaternium-11, Polyquaternium-14, Polyquaternium-16, Polyquaternium-17, Polyquaternium-18, Polyquaternium-22, Polyquaternium-24, Polyquaternium-27, Polyquaternium-28, Polyquaternium-32, Polyquaternium-33, Polyquaternium-37, Polyquaternium-39, Polyquaternium-44, Polyquaternium-46, Polyquaternium-53, Polyquaternium-55, Polyquaternium-64, Polyquaternium-67, Polyquaternium-68, Polyquaternium-69 and/or Polyquaternium-86, and mixtures thereof, preferably in a total quantity of from about 0.01 to about 2 wt %, preferably from about 0.1 to about 1.5 wt %, more preferably from about 0.5 to about 1.0 wt %, each relative to the weight of the composition. Particularly preferred compositions as contemplated herein are characterized in that they contain a mixture of Polyquaternium-4 and Polyquaternium-11, and most particularly preferably in a total quantity of from about 0.01 to about 2 wt %, preferably from about 0.1 to about 1.5 wt %, more preferably from about 0.5 to about 1.0 wt %, relative to the weight of the respective composition. The presence of at least one of said cationic polymers can enhance the color absorption and/or the desired foaming properties.

Additionally, it was found surprisingly that the presence of at least one nonionic polyvinyl pyrrolidone/vinyl acetate polymer in a total quantity from about 0.1 to about 2.0 wt %, preferably from about 0.2 to about 1.5 wt %, particularly preferably from about 0.4 to about 1.0 wt %, each relative to the weight of the composition, can have a beneficial effect on color absorption and/or the desired foaming properties. Further preferred compositions as contemplated herein are therefore characterized in that they contain at least one nonionic polyvinyl pyrrolidone/vinyl acetate polymer in a total quantity from about 0.1 to about 2.0 wt %, preferably from about 0.2 to about 1.5 wt %, particularly preferably from about 0.4 to about 1.0 wt %, relative to the weight of the composition in each case.

Since the compositions as contemplated herein are intended to be sprayable, in an extremely preferred embodiment, they contain no fatty components with a melting point in the range about 28-80° C. Examples of fat components with a melting point in the range about 28-80° C. which undesirable as contemplated herein are linear saturated 1-alkanols having 12-30 carbon atoms and esters of mono- and polyvalent C1-C10-alkanols and C8-C30-alkanoic acids, and waxes. The abovementioned nonionic surfactants may have melting points in the range about 28-80° C. have, but are not among the fatty components listed above. The abovementioned fat components having a melting point in the range about 28-80° C. differ from the nonionic surfactants by the absence of hydrophilic groups.

The inventive compositions preferably have a viscosity in the range of about 50-1000 mPas, particularly preferably about 100-700 mPas, extremely preferably about 150-300 mPas, each being measured at 20° C. in a MV2 type Haake viscometer at a speed of 8 rpm. Negative effects on the foaming behavior were also observed for aliphatic C1-C6 alcohols such as ethanol, isopropanol, polyols selected from C2-C9 alkanols with 2-6 hydroxyl groups such as ethylene glycol, glycerol, propylene glycol, 1,3-butylene glycol, and polyethylene glycols having at least 2 ethylene oxide units, e.g., PEG-3, PEG-4, PEG-6, PEG-7, PEG-8, etc. Therefore, preferred compositions contain no aliphatic C1-C6 alcohols, no C2-C9 alkanols with 2-6 hydroxyl groups and no polyethylene glycols with at least 2 ethylene oxide units. The polyethylene glycols with at least 2 ethylene oxide units excluded here consist only of ethylene oxide units and contain no hydrophobic moieties. Although the compositions can be adjusted to an acidic pH as contemplated herein, it may still be necessary to use small quantities of alkalizing agents for fine adjustment of the pH. The alkalizing agents that may optionally be used to adjust the preferred pH values may be selected from the group of ammonia, alkanolamines, basic amino acids, and inorganic alkalizing compounds such as alkaline (earth) metal hydroxides, alkaline (earth) metal metasilicates, alkaline (earth) metal phosphates and alkaline (earth) metal hydrogen phosphates. Preferred inorganic alkalizing agents are sodium hydroxide, potassium hydroxide, sodium silicate and sodium metasilicate. Organic alkalizing agents that are usable as contemplated herein are preferably chosen from monoethanolamine, 2-amino-2-methyl propanol and triethanolamine. The basic amino acids which can be used as inventive alkalizing agents are preferably selected from the group of arginine, lysine, ornithine and histidine, most preferably arginine. However, it was found during the research associated with the present disclosure that further inventively preferred compositions are characterized in that they also contain an organic alkalizing agent. An embodiment of the first object as contemplated herein is characterized in that the composition additionally contains at least one alkalizing agent selected from the group of ammonia, alkanolamines and basic amino acids, particularly ammonia, monoethanolamine and arginine or its cosmetically acceptable salts.

A second object of the present disclosure is a hair dye product comprising a spray can and, packed therein, an inventive or inventively preferred colorant and at least one propellant, wherein the weight ratio of colorant to propellant is in the range from about 5:95 to about 95:5, preferably about 50:50, more preferably about 80:20.

Preferred propellants (propellant gases) are propane, propene, n-butane, isobutane, isobutene, n-pentane, pentene, isopentane, iso-pentene, methane, ethane, dimethyl ether, nitrogen, air, oxygen, nitrous oxide, 1,1,1,3-tetrafluoroethane, heptafluoro-n-propane, perfluoroethane, monochlorodifluoromethane, 1,1 difluoroethane, both individually and in combination. Hydrophilic propellants such as carbon dioxide may be used advantageously within the scope of the present disclosure if the proportion of hydrophilic gases is selected to be small and the lipophilic propellant gas (e.g. propane/butane) is present in excess. Particularly preferred are propane, n-butane, isobutane and mixtures of these propellant gases. Particularly preferred propellant mixtures are LPG ("Liquefied Petroleum Gas").

Pressurized containers which are usually equipped either with a suitable, possibly mechanical pressure accumulator, or also a propellant gas inside the container which thus place the interior of the container under pressure may be cited as examples of dispensers as contemplated herein with integrated pressure source. Such pressurized containers usually have suitable valve devices to discharge the preparation located inside the pressurized container during a corresponding valve actuation. Such pressurized containers are already known in the form of aerosol dispensers for various cosmetic applications, particularly those associated with gas-phase and/or liquid propellants, for example as hair styling spray, hair coloring preparations, deodorant spray, shaving cream/gel etc.

Alternatively, manually operated dispensers which are actuated solely by the force applied by the user to cause a foaming discharge of the preparation may also be used as contemplated herein. With these designs, an additional pressure source such as a propellant may advantageously be omitted, which is desirable in particular for cost and sustainability reasons.

Besides expelling the hair dye preparation from the preparation reservoir towards the dispensing aperture, these kinds of manually operable foam dispensers also ensure that the hair dye preparation is foamed correspondingly. During this foaming or foam formation, the hair dye preparation is generally mixed with a gas-phase component, particularly air. Specifically, a foaming device is provided for this purpose, which accomplishes this.

According to a first variant of a manually operable dispenser, the dispenser is designed as a shake dispenser, with at least one reservoir for accommodating the hair dye preparation and an associated dispensing device for dispensing the hair dye preparation in foamed form. In particular, the dispensing device is connected to the reservoir so as to be detachable. The actual foaming occurs inside the shake dispenser when the hair dye preparation is agitated in the reservoir. In this respect, the shake dispenser in conjunction with the corresponding dispenser movement constitutes the aforementioned foaming device. Following this kind of foaming, the foamed hair dye preparation can then be dispensed via the dispenser device.

Another practical dispenser variant is created when the foam dispenser is designed as a compression or squeezed foam dispenser. Besides the at least one reservoir for holding the hair dye preparation, such a squeezed foam dispenser has a corresponding application device inside of which the foaming and subsequent dispensing of the hair dye preparation takes place. The actual transport of the hair dye preparation from the reservoir effected by exerting a force on the flexible reservoir wall. Here, the reversible deformation of the reservoir wall causes pressure to build up inside the reservoir, with the result that the hair dye preparation is expelled from the reservoir. Therefore it is necessary to make the reservoir wall sufficiently flexible and reversibly deformable. This is ensured by designing the thickness of the reservoir wall appropriately for the application in conjunction with selection of an appropriate material for the selection for the reservoir wall. The reservoir wall of a corresponding squeezed foam dispenser is preferably made from a polyolefin, such as polypropylene (PP), high density polyethylene (HDPE), medium density polyethylene (MDPE), low density polyethylene (LDPE), linear low density polyethylene (LLDPE). Of these, polypropylene (PP) is preferred.

The application device of such a squeezed foam dispenser also comprises a corresponding foaming device for foaming the hair dye preparation. The foaming device is able to mix a quantity of the preparation with a quantity of gas in a suitable dosing ratio to form the desired foam consistency of the hair dye preparation. For this, a drawn stream of the preparation is usually mixed with an aspirated stream of gas inside a mixing chamber of the foaming device, where they are mixed by fluidic turbulence. Particularly preferably, air serves as the gas-phase component for foaming and is either fed directly from the reservoir or from the environment.

The basic mode of operation of such squeezed foam dispensers is also described in the documents WO 2007/086730 A2/A3 and EP 1237660 B1. An inventive squeezed foam dispenser can also be fabricated according to these patent documents. In particular, the squeezed foam dispenser as contemplated herein in accordance with the disclosure of EP 1237660 B1 can be designed so that the squeezed foam dispenser can be used in a substantially upright position and upside down.

Similarly, the dispenser may be designed as a pump foam dispenser having at least one reservoir to accommodate the hair dye preparation and an application device, in which case the application device includes a pumping device for conveying both the hair dye preparation and the gas-phase component, preferably air, and also a corresponding foaming device. The details of the mode of operation and the structural design of such pump-foam dispensers are disclosed in patent documents WO 2007/083206 A1 or WO 2007/091882 A1 among others. In particular, the pump foam dispenser as contemplated herein may be designed according to the disclosure of these documents.

The notes provided as contemplated herein and inventively preferred compositions apply mutatis mutandis to further preferred embodiments of the hair dye product as contemplated herein. However, the dyes as contemplated herein or preferred as contemplated herein may also be discharged advantageously as foam from a non-aerosol foam dispenser and used in a hair dyeing method as contemplated herein. A further object of the present disclosure is therefore a hair dye product comprising a non-aerosol foam dispenser and, included therein, an inventive or inventively preferred colorant.

A third object of the present disclosure is a method for dyeing keratinous fibers in which a composition is discharged as a foam from a dispenser, preferably from a spray can or from a non-aerosol foam dispenser, the foam thus obtained is then spread onto the keratinous fibers, and then remains on the keratinous fibers for a period from about 30 seconds to about 60 minutes, preferably from about 5 to about 45 minutes, and is then rinsed off the keratinous fibers. The notes provided above regarding the inventive and inventively preferred compositions apply mutatis mutandis to further preferred embodiments of the method as contemplated herein.

EXAMPLES

1. Formulation Examples

The following formulations were prepared—unless otherwise stated all, data relates to the percentage by weight of the active substance. The samples marked with "V" are comparison compositions, samples marked with "E" are inventive compositions.

Colorant

| Content | V1 (wt %) | E1 (wt %) | E2 (wt %) | E3 (wt %) | V2 (wt %) | V3 (wt %) | V4 (wt %) |
|---|---|---|---|---|---|---|---|
| Acid Black no. 1 | 0.2 | 0.2 | 0.2 | 0.2 | 0.2 | 0.2 | 0.2 |
| Acid Orange 7 | 0.2 | 0.2 | 0.2 | 0.2 | 0.2 | 0.2 | 0.2 |
| Acid Violet 43 | 0.1 | 0.1 | 0.1 | 0.1 | 0.1 | 0.1 | 0.1 |
| Benzyl alcohol | 10 | — | 1 | 2 | 3 | 4 | 5 |
| Propylene carbonate | — | 10 | 9 | 8 | 7 | 6 | 5 |
| Poly quaternium-4 | 0.319 | 0.319 | 0.319 | 0.319 | 0.319 | 0.319 | 0.319 |
| PVP/VA copolymer (60/40) | 0.75 | 0.75 | 0.75 | 0.75 | 0.75 | 0.75 | 0.75 |
| Polyquaternium-11 | 0.3 | 0.3 | 0.3 | 0.3 | 0.3 | 0.3 | 0.3 |
| Sodium benzoate | 0.319 | 0.319 | 0.319 | 0.319 | 0.319 | 0.319 | 0.319 |
| Quaternium-52 | 0.213 | 0.213 | 0.213 | 0.213 | 0.213 | 0.213 | 0.213 |
| Cetyltrimonium chloride | 0.27 | 0.27 | 0.27 | 0.27 | 0.27 | 0.27 | 0.27 |
| Lactic acid | 0.08 | 0.08 | 0.08 | 0.08 | 0.08 | 0.08 | 0.08 |
| PEG 40 Hydrogenated Castor Oil | 0.425 | 0.425 | 0.425 | 0.425 | 0.425 | 0.425 | 0.425 |
| Fragrance | 0.2 | 0.2 | 0.2 | 0.2 | 0.2 | 0.2 | 0.2 |
| Water (dist.) | To 100 | To 100 | To 100 | To 100 | To 100 | To 100 | To 100 |
| Foam stability | Poor | Good | Good | Good | Poor | Poor | Poor |

2. Application

Each colorant was discharged as a foam from a non-aerosol dispenser or from a propellant gas dispenser and applied to damaged hair (Kerling 6-0, previously damaged) (4 g dye per 1 g hair), left on the hair for 40 minutes and then rinsed out with water (32° C.). The hair was then stored for 24 hours at 25° C. and 25% relative humidity. All hair samples exhibited excellent coloring properties.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic composition for dyeing keratinous fibers, the cosmetic composition comprising:
   water; and
   from about 6 to about 12 wt % organic solvent relative to the weight of the composition, wherein the organic solvent comprises;
      from about 80 to about 100 wt % propylene carbonate, and
      from about 0 to about 20 wt % benzyl alcohol;
   wherein the cosmetic composition has:
      a pH value in the range from about 1.0 to about 5.5,
      at least one acid directly absorbed dye, and
      at least one nonionic ethoxylated surfactant in a total quantity of from about 0.1 to about 1 wt %, relative to the weight of the cosmetic composition, wherein the at least one nonionic ethoxylated surfactant is selected from the group of ethylene oxide adducts to saturated or unsaturated, linear or branched fatty alcohols and fatty acids and to glycerol fatty acid esters, each with about 2 to about 60 moles ethylene oxide per mole fatty alcohol or fatty acid or glycerol fatty acid esters, and combinations thereof.

2. The cosmetic composition according to claim 1, wherein the cosmetic composition comprises at least one acid directly absorbed dye from the group of Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 18, Acid Red 27, Acid Red 33, Acid Red 35, Acid Red 51, Acid Red 52, Acid Red 73, Acid Red 87, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 7, D&C Yellow 8, D&C Orange 4, D&C Green 5, D&C Orange 10, D&C Orange 11, D&C Red 21, D&C Red 27, D&C Red 33, D&C Violet 2, D&C Brown 1, and combinations thereof.

3. The cosmetic composition according to claim 1, wherein the cosmetic composition comprises at least one of the following combinations of acid directly absorbed dyes: Acid Yellow 1/Acid Orange 7; Acid Yellow 3/Acid Orange 7; Acid Yellow 9/Acid Orange 7; Acid Yellow 17/Acid Orange 7; Acid Yellow 23/Acid Orange 7; Acid Yellow 36/Acid Orange 7; Acid Yellow 121/Acid Orange 7; Acid Red 14/Acid Orange 7; Acid Red 18/Acid Orange 7; Acid Red 27/ Acid Orange 7; Acid Red 33/Acid Orange 7; Acid Red 35/Acid Orange 7; Acid Red 51/Acid Orange 7; Acid Red 52/Acid Orange 7; Acid Red 73/Acid Orange 7; Acid Red 87/Acid Orange 7; Acid Red 95/Acid Orange 7; Acid Red 184/Acid Orange 7; Acid Red 195/Acid Orange 7; Acid Violet 43/Acid Orange 7; Acid Violet 49/Acid Orange 7 or Acid Violet 50/Acid Orange 7.

4. The cosmetic composition according to claim 1, wherein the cosmetic composition comprises one or more acid directly absorbed dyes in a total quantity of from about 0.01 to about 5.5 wt %, relative to the weight of the composition.

5. The cosmetic composition according to claim 1, wherein the cosmetic composition has a pH value from about 1.5 to about 4.7.

6. The cosmetic composition according to claim 1, wherein the cosmetic composition comprises about 4.8 to about 12 wt % of propylene carbonate and 0 to about 2.4 wt % of benzyl alcohol, relative to the weight of the cosmetic composition.

7. The cosmetic composition according to claim 1, wherein the cosmetic composition comprises at least one cationic surfactant in a total quantity of from about 0.1 to about 2% by weight relative to the weight of the cosmetic composition.

8. The cosmetic composition according to claim 1, wherein the cosmetic composition comprises at least one cationic polymer in a total quantity of from about 0.01 to about 2 wt %, relative to the weight of the cosmetic composition.

9. The cosmetic composition according to claim 1, wherein the cosmetic composition comprises at least one nonionic polyvinyl pyrrolidone/vinylacetate polymer in a total quantity of from about 0.1 to about 2.0 wt %, relative to the weight of the cosmetic composition.

10. Hair dye product, comprising a spray can and, packed therein, a cosmetic composition and at least one propellant, wherein the weight ratio of colorant to propellant is in the range of from about 5:95 to about 95:5, and wherein the cosmetic composition comprises:
water; and
from about 6 to about 12 wt % organic solvent relative to the weight of the composition, wherein the organic solvent comprises:
from about 80 to about 100 wt % propylene carbonate, and
from about 0 to about 20 wt % benzyl alcohol;
wherein the cosmetic composition has:
a pH value in the range from about 1.0 to about 5.5, and
at least one acid directly absorbed dye.

11. Method for dyeing keratinous fibers, the method comprising:
discharging a cosmetic composition according to claim 1 as a foam from a dispenser,
spreading the foam onto the keratinous fibers,
remaining the foam on the keratinous fibers for a period of from about 30 seconds to about 60 minutes, and
rinsing the foam out of the keratinous fibers.

12. The cosmetic composition according to claim 6, wherein the cosmetic composition is free of 2-phenoxyethane-1-ol, benzyloxyethanol, and N-alkylpyrrolidone.

13. The cosmetic composition according to claim 7, wherein the at least one cationic surfactant is selected from the group of C10-C22 alkyltrimethylammonium chlorides and combinations thereof.

14. The cosmetic composition according to claim 13, wherein the at least one cationic surfactant is selected from the group of behenyl trimethyl ammonium chloride, stearyl trimethyl ammonium chloride, cetyl trimethyl ammonium chloride, quaternium-52, and combinations thereof.

15. The cosmetic composition according to claim 1, wherein the at least one nonionic ethoxylated surfactant is selected from the group of PEG-40 Hydrogenated Castor Oil, PEG-60 Hydrogenated Castor Oil, and a combination thereof.

16. The cosmetic composition according to claim 8, wherein the at least one cationic polymer is selected from the group of Polyquaternium-1, Polyquaternium-2, Polyquaternium-3, Polyquaternium-4, Polyquaternium-5, Polyquaternium-6, Polyquaternium-7, Polyquaternium-8, Polyquaternium-9, Polyquaternium-10, Polyquaternium-11, Polyquaternium-14, Polyquaternium-16, Poly quaternium-17, Poly quaternium-18, Polyquaternium-22, Polyquaternium-24, Polyquaternium-27, Polyquaternium-28, Polyquaternium-32, Polyquaternium-33, Polyquaternium-37, Polyquaternium-39, Polyquaternium-44, Polyquaternium-46, Polyquaternium-53, Polyquaternium-55, Polyquarternium-64, Polyquaternium-67, Polyquaternium-68, Polyquaternium-69, Polyquaternium-86, and combinations thereof.

17. The cosmetic composition according to claim 16, wherein the at least one cationic polymer is selected from mixtures of Polyquaternium-4 and Polyquaternium-11.

18. The cosmetic composition according to claim 5, wherein the cosmetic composition has a pH value from about 1.8 to about 2.5.

* * * * *